US012211333B1

(12) United States Patent
Stafford et al.

(10) Patent No.: US 12,211,333 B1
(45) Date of Patent: Jan. 28, 2025

(54) PROTECTIVE COVERINGS FOR DISPLAYS USED IN OUTDOOR ENVIRONMENTS

(71) Applicant: Amazon Technologies, Inc., Seattle, WA (US)

(72) Inventors: Emily Rose Stafford, Kirkland, WA (US); Joe Kraisorn, Ridgewood, NJ (US); Thomas Dutcher, Seattle, WA (US); Geoffrey Charles Adleman, Shoreline, WA (US); Kevin John Donahoe, Burien, WA (US); James Harvey, Seattle, WA (US)

(73) Assignee: Amazon Technologies, Inc., Seattle, WA (US)

( * ) Notice: Subject to any disclaimer, the term of this patent is extended or adjusted under 35 U.S.C. 154(b) by 24 days.

(21) Appl. No.: 18/067,320

(22) Filed: Dec. 16, 2022

(51) Int. Cl.
*B60J 7/047* (2006.01)
*A61L 2/10* (2006.01)
(Continued)

(52) U.S. Cl.
CPC .................. *G07C 9/33* (2020.01); *A61L 2/10* (2013.01); *A61L 2/24* (2013.01); *B08B 1/165* (2024.01);
(Continued)

(58) Field of Classification Search
CPC . G07F 11/62; G07F 17/12; G07F 7/06; G07F 9/001; G07F 11/005; G07F 11/04; G07F 11/163; G07F 17/0042; G07F 17/0092; G07F 17/04; G07F 17/10; G07F 9/002; G07F 9/10; G07F 19/203; G07F 19/2055; G07F 7/1033; G07F 9/009; G07F 11/1657; G07F 11/24; G07F 11/52; G07F 11/54; G07F 13/10; G07F 17/0014; G07F 17/0021; G07F 17/13; G07F 17/248; G07F 7/069; G07F 9/023; G07F 9/06; G07F 9/105; G06K 7/10297; G06Q 20/1085; G06Q 20/4012; G07D 11/14; G07D 11/60; A47B 2031/006; A47B 2067/025;
(Continued)

(56) References Cited

U.S. PATENT DOCUMENTS 11,540,677 B1 * 1/2023 Donahue ................. H01F 7/081
11,617,436 B1 * 4/2023 McNannay ........... A61J 7/0418
109/44

(Continued)

*Primary Examiner* — Dionne Pendleton
(74) *Attorney, Agent, or Firm* — Eversheds Sutherland (US) LLP

(57) ABSTRACT

A protected covering for displays used in outdoor environments is provided. Particularly, the protective covering may be provided over a display screen of a delivery locker system. The protective covering may protect the display screen from overheating from sun rays and other heat sources that may exist in an external environment. The protective covering may be configured to be moved between a first position in which the protective covering is covering the display screen and a second position in which the protective covering is not covering the display screen. This allows the protective covering to protect the display screen when not in use but also allow a user to move the protective covering to access the display screen when needed. The protective covering may also include magnets to secure the protective covering to the delivery locker system in the first position or the second position.

18 Claims, 6 Drawing Sheets

(51) Int. Cl.
*A61L 2/24* (2006.01)
*B08B 1/16* (2024.01)
*B08B 1/30* (2024.01)
*G07C 9/33* (2020.01)
*H01F 7/06* (2006.01)

(52) U.S. Cl.
CPC ............... *B08B 1/30* (2024.01); *H01F 7/064* (2013.01); *A61L 2202/11* (2013.01); *A61L 2202/121* (2013.01); *A61L 2202/14* (2013.01); *A61L 2202/17* (2013.01)

(58) Field of Classification Search
CPC .. A47B 31/00; A47B 67/02; A47G 2029/145; A47G 2029/147; A61J 1/03; A61J 1/035; A61J 1/16; A61J 1/165; A61J 2200/30; A61J 2200/70; A61J 2205/60; A61J 7/0418; A61J 7/0481; B25J 11/008; B25J 9/0096; B25J 9/102; B25J 9/1682; B25J 9/1697; B60J 5/101; B60J 7/0435; B60J 7/047; B65G 1/0478; E05G 1/10; A01B 63/10; A01B 63/1006; A01B 63/112; A47K 13/10; D06F 23/04; D06F 37/28; D06F 39/088; D06F 39/14; E03C 1/025; F15B 11/08; F15B 13/015; H01F 7/081; H01F 7/16

See application file for complete search history.

(56) References Cited

U.S. PATENT DOCUMENTS

| | | | |
|---|---|---|---|
| 2015/0356801 A1* | 12/2015 | Nitu | G07F 9/001 340/5.61 |
| 2018/0247286 A1* | 8/2018 | Denny | G07F 19/2055 |
| 2020/0263344 A1* | 8/2020 | Leibman | E03C 1/025 |
| 2021/0076555 A1* | 3/2021 | Greif | A01B 63/1006 |
| 2021/0387103 A1* | 12/2021 | Chung | G02B 27/0176 |
| 2023/0385753 A1* | 11/2023 | Nere | G06Q 10/0836 |

* cited by examiner

PROTECTIVE COVERINGS FOR DISPLAYS USED IN OUTDOOR ENVIRONMENTS

BACKGROUND

Delivery locker systems provide a convenient option for customers or delivery carriers who require a temporary and secure storage location for delivery packages. For example, a user may not be home during a delivery time and may desire the package to be temporarily delivered to one of these secure lockers for a later pickup. As another example, a customer may be traveling and not located near a permanent residential address for delivery. These delivery locker systems may include display screens that a customer may use to enter a code to unlock the particular locker in which their package is stored. However, these delivery locker systems are often provided in an outdoor environment. As such, the display screens may be subject to sun rays and other heat sources that may cause the display screens to overheat and cause tactile and physical issues. For example, the display screens may be too hot for a user to interact with to enter a code to receive a package.

BRIEF DESCRIPTION OF THE DRAWINGS

The detailed description is set forth with reference to the accompanying drawings. The drawings are provided for purposes of illustration only and merely depict example embodiments of the disclosure. The drawings are provided to facilitate understanding of the disclosure and shall not be deemed to limit the breadth, scope, or applicability of the disclosure. In the drawings, the left-most digit(s) of a reference numeral may identify the drawing in which the reference numeral first appears. The use of the same reference numerals indicates similar, but not necessarily the same or identical components. However, different reference numerals may be used to identify similar components as well. Various embodiments may utilize elements or components other than those illustrated in the drawings, and some elements and/or components may not be present in various embodiments. The use of singular terminology to describe a component or element may, depending on the context, encompass a plural number of such components or elements and vice versa.

DETAILED DESCRIPTION

Figure 1:
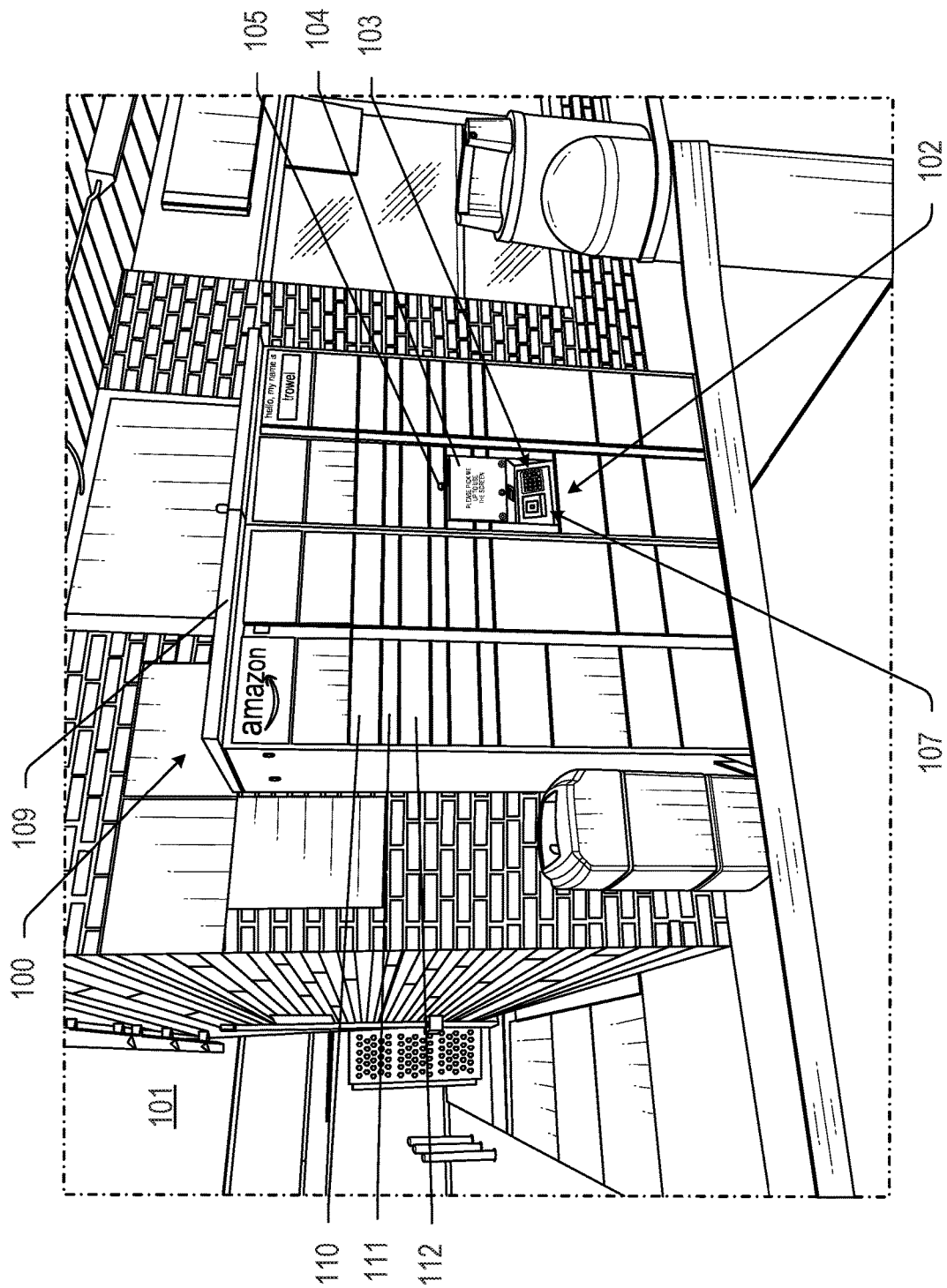
FIG. 1 illustrates an example delivery locker system within an environment in accordance with one or more example embodiments of the disclosure.

This disclosure relates to, among other things, protective coverings for displays used in outdoor environments. Particularly, the protective covering (which may be referred to interchangeably as a "cover" herein) is provided over a display screen included on a delivery locker system. The protective covering reduces the exposure of the display screen to sun rays and other heat sources from the external environment to prevent the display screen from overheating due to overexposure to such heat sources.

The protective cover may include any number of different types of materials. For example, the protective cover may be provided in the form of a shade made of a fabric or another type of lightweight material. Using a lightweight material may allow a user to more easily move the protective covering away from and back in front of the display screen. However, the protective covering may also include any other type of material as well. As another example, the protective covering may include a more rigid material, such as a hard plastic or glass. The use of a more rigid material may provide the benefit of providing additional protection to the display screen from physical damage that may result from environmental conditions, such as weather conditions, debris projected towards the delivery locker system, etc. The protective covering may also be translucent or transparent to allow for the display screen to be viewed when the protective cover is in the down position and covering the display screen. However, it may also be desirable for the protective cover to be opaque such that the display screen is not visible until the protective covering is moved to the up position as well. It should be noted that the "up" and "down" positions may also be generally referred to as a "first" and/or "second" position herein as well (the first and second positions may refer to either the up or down position).

In one or more embodiments, the protective covering may also include multiple coverings including different types of materials. For example, the protective covering may normally be provided in the form of a fabric (or any other type of less rigid material), but a more rigid, second covering may be deployed over the display screen based on certain triggering conditions. For example, if the delivery locker system senses that a high velocity impact from an object is imminent, the delivery locker system may deploy the more rigid protective cover to prevent the object from impacting and damaging the display screen. This determination may be made using one or more sensors provided on the protective covering and/or the delivery locker system (e.g., cameras, light detection and ranging (lidar), radio detection and ranging (radar), proximity sensors, etc.). In some cases, an algorithm may also be used to identify situations where the more rigid protective covering should be deployed. For example, the algorithm may include machine learning (or any other type of artificial intelligence) that may be used to detect aggressive user behavior proximate to the delivery locker system, high velocity objects proximate to the delivery locker system (as aforementioned), and/or any other types of conditions that may potentially result in damage to the display screen.

The protective covering may also include one or more magnets used to removably affix the protective covering to the delivery locker system when the protective covering is lifted away from the display screen to allow a user to interact with the display screen. Similarly, the one or more magnets may be used to removably affix the protective covering to the delivery locker system when the protective covering is in the down position (e.g., covering the display screen) as well. This may be advantageous to maintain the protective covering in the down position when the display screen is not in use by a user. For example, if the protective covering is not removably affixed to the delivery locker system, conditions such as wind may cause the protective covering to partially or fully move away from the display screen.

The one or more magnets may include individual magnets provided at various positions on the protective covering. For example, the one or more magnets may be provided at the bottom corners of the protective covering and/or at any other combination of positions on the protective covering. In one or more embodiments, the one or more magnets may also be provided as a continuous strip at a bottom edge of the protective covering. The one or more magnets may be provided on the interior side of the protective covering, the exterior side of the protective covering, or both the interior side and the exterior side of the protective covering. Depending on the strength of the one or more magnets, the one or more magnets may only need to be provided on one side of the protective covering and may still be capable of affixing to the delivery locker system in both the up and down positions (as shown in the figures, the side of the protective covering that is facing the delivery locker system may flip when the protective covering is in the up position and in the down position). However, in some cases, the one or more magnets may need to be provided on both sides of the protective covering for the magnets to affix to the delivery locker system in the up and the down position. These are just a few examples of configurations of magnets provided on the protective covering and are not intended to be limiting.

In one or more embodiments, the magnets may also specifically be electromagnets. Using electromagnets allows for the magnets included on the protective covering to be selectively magnetized or demagnetized at any given time. This is advantageous in scenarios where a user moves the protective covering to the up position and affixes the magnets to a side of the delivery locker system, but fails to return the protective covering back to the down position after using the display screen. To prevent this scenario, the electromagnets may be demagnetized after a threshold period of time such that the electromagnets then release from the delivery locker system and the protective covering falls back to the down position and covers the display screen. Additionally, in some cases, the trigger for demagnetizing the electromagnets may also include a determination that a user is not proximate to and/or interacting with the display screen. This determination may be made, for example, using a camera or other types of sensors included on the delivery locker system, the display screen, and/or the protective covering. This may prevent a further scenario where a user affixes the magnets to the delivery locker system to interact with the display screen, but remains at the delivery locker system for more than the threshold period of time. In some cases, the electromagnets may be re-magnetized when the protective cover is back in the down position.

The electromagnets may also be selectively demagnetized when the protective covering is in the down position and it is determined that a user is proximate to the delivery locker system or approaching the delivery locker system. This may allow for the user to more easily move the protective covering from the down position to the up position.

The protective covering may also include a mechanism used to clean the display screen. For example, a wiper mechanism (e.g., similar to a windshield wiper found on an automobile, depicted as wiper 205 in FIG. 2) may be provided on an interior side (e.g., the side of the protective covering that is facing the display screen when the protective covering is in the down position) of the protective covering. When the protective covering is in a "down" position and covering the display screen, the wiper mechanism may be used to actuate between two positions to clean dust and debris (and other contaminants) from the display screen. Any other type of mechanism may also be used to clean the display screen and the mechanism may also be provided at any other location on the protective covering. The mechanism may also be provided on the delivery locker system and/or the display screen itself.

Another example of a cleaning mechanism may include one or more ultraviolet light (UV) sources (also referred to herein as a "UV light assembly"). UV radiation is a known disinfectant for air, water, and nonporous surfaces, for example. The one or more UV light sources may be activated after the protective covering is returned to the down position and is covering the display screen. Thus, the one or more UV light sources may also be provided on an interior side of the protective covering. The one or more UV light sources may similarly be provided on the delivery locker system and/or the display screen as well. The one or more UV light sources may serve to sanitize the displays screen between customer uses and/or at any other intervals. For example, the one or more UV light sources may instead be configured to activate periodically based on an amount of time having elapsed rather than between individual customer uses of the display screen.

The protective covering, the display screen, and/or the delivery locker system may also include a cooling system. The cooling system may be configured to activate when it is determined that the display screen has reached a threshold temperature. For example, the cooling system may include one or more fans that may blow air across the display screen to cool the display screen. The cooling system may also include any other type of cooling mechanism as well.

The protective covering may include messaging that may be used to provide information to a user. For example, the messaging may provide instructions to the user to lift the protective covering to access the screen. The messaging may also indicate to the user to return the protective covering back to the down position when the user is no longer using the display screen. In some cases, the messaging may be printed directly on the protective covering. In other cases, the messaging may be digital messaging that is presented through a display that is provided on the protective covering. For example, display may be a seven-segment display, a light emitting diode (LED) display, an e-ink display, and/or any other type of display. The messaging may also be dynamic and may provide a number of different types of information to a user. For example, if the temperature of the display screen is above a threshold temperature (as described below), the display may indicate to the use that the delivery locker system may need to be accessed using a method other than an interaction with the display screen.

The protective covering may also be configured to provide information to a user in any other form beyond text or visual messaging as well. For example, the protective covering may include one or more speakers that are configured to emit audible information to a user. For example, the speakers may emit instructions for the user to lift the protective covering to access the display screen. As another example, when it is determined that the user has finished using the display screen and/or the delivery locker system (for example, when the user closes a locker door after removing a package, etc.), the speakers may provide an audible instruction for the user to replace the protective cover over the display screen. The speakers may similarly be provided on the display screen and/or the delivery locker system as well.

In one or more embodiments, the protective covering may also include automated functionality to report when the protective covering detects that is requires a repair or replacement. For example, the protective covering may be configured to determine, using various sensors, damage to the protective covering. An indication of a need for repair or replacement may be transmitted to a remote device or system, such as a technician device. In a similar way, the protective covering may also be configured to detect a need for repair or replacement of the display screen and/or any other component of the delivery locker system as well. Likewise, the display screen and/or any other component of the delivery locker system may be configured to detect that the protective covering requires a repair or replacement. As one non-limiting example, a camera may be provided on the delivery locker system that may capture images and/or video of the protective covering. In this example, the delivery locker system may identify when the protective covering requires repair or replacement based on the images and/or video.

In one or more embodiments, the protective covering may also be configured to automatically move between the up position and the down position. For example, if the protective covering is provided as a rigid material, the protective covering may be affixed to the delivery locker system on a hinge and the protective covering may be rotated about the hinge between the up and down position using a motor or servo. As another example, the protective covering may be configured to automatically retract in a similar manner to a window shade. The protective covering may also be configured to move between a first position in which the protective covering is covering the display screen and a second position in which the protective covering is not covering the display screen (or only partially covering the display screen) using any other mechanism.

The automated actuation of the protective covering may be facilitated based on any number of triggering conditions. For example, one or more sensors (such as a camera, lidar, radar, a proximity sensor, etc.) may detect when a user is approaching the delivery locker system. Based on this determination, the delivery locker system may automatically actuate the protective covering to an up position to allow the user access to the display screen. As another example, the actuation of the protective covering may be performed based on a user action, such as a press of a button an audible command from the user, a gesture performed by the user, etc.

To further mitigate or prevent the display screen from exceeding a threshold temperature, the display screen may also be configured to automatically tilt before and after use. For example, when the displays screen is in use, the display screen may rotate vertically or tilt upwards or in a direction that is directly facing the user to provide case of interaction. When it is determined that the user is no longer using the display screen, the display screen may then tilt downwards (or in a direction such that the display screen is facing away from direct sunlight) to reduce the solar load on the display screen. The display screen and/or delivery locker may also include a sun visor (or similar component) positioned above the display screen to provide further protection from solar rays while the protective covering is not in the down position.

In one or more embodiments, the delivery locker system itself may also be configured to automatically perform certain actions based on the temperature of the display screen. For example, in some instances, the display screen may still reach a certain threshold temperature or may overhead, such as when the protective covering is left within an up position and/or for any other reason. In such instances, the delivery locker system may be configured to automatically perform certain actions to allow a user to still be able to access the contents of a delivery locker even if the temperature of the display screen is high enough that the display screen is unusable or is undesirable for a user to touch.

As one example, the delivery locker system may be equipped with a Bluetooth device (the device may include a Bluetooth radio, for example). Rather than interacting with the display screen, a user may perform an action with respect to the delivery locker system to enable a Bluetooth connection between the delivery locker system and a user device, such as a smartphone. For example, the user may press a button on the locker to enable the Bluetooth connection. The Bluetooth connection may also be enabled in any other suitable manner as well.

Once the Bluetooth connection is established, the delivery locker system may verify the identity of the user and/or may otherwise determine that the user is authorized to access a particular locker of the delivery locker system. Based on a determination that the user is authorized, the delivery locker system may automatically open to allow the user to access the interior of the delivery locker system to obtain a package. In some cases, the delivery locker system may open a specific delivery locker including the package associated with the user rather than providing the user access to all of the interior of the delivery locker system. Although reference is made to Bluetooth, any other similar type of short range communication protocol may similarly be used (for example, near field communications (NFC), etc.).

As another example, the delivery locker system may include a biometric system. For example, the biometric system may include a fingerprint reader, a palm reader, a facial-recognition system, and/or any other type of biometric system. Similar to the Bluetooth device, the biometric system may be used to verify the identity of the user proximate to the delivery locker system. If the biometric system determines that the user is authorized to access the delivery locker system, the delivery locker system may provide such access by unlocking and/or otherwise providing the user access to one or more of the lockers included within the delivery locker system. These are just a few examples of mechanisms that may allow the delivery locker system to provide user access when the displays screen is above the threshold temperature and are not intended to be limiting.

The display screen may also take certain actions to reduce the temperature of the display screen. As aforementioned, the display screen, protective covering, and/or delivery locker system may include a cooling system. This cooling system may be activated when the display screen is determined to reach the threshold temperature. As another example, the display screen may be transitioned into a lower power mode of operation. For example, the display screen may be dimmed or turned off and/or other functionality of the display screen may be reduced or temporarily disabled until the temperature of the display screen falls below the threshold temperature value.

Turning to the figures, FIG. 1 illustrates an example delivery locker system 100 within an environment 101 (which may also be referred to as an "external environment" or an "outdoor environment") in accordance with one or more example embodiments of the disclosure.

The delivery locker system 100 may include a housing 109 in which one or more individual lockers (for example, locker 110, locker 111, locker 112, and/or any other number of lockers shown in the figure or otherwise) are contained. The individual lockers may be configured to temporarily store different packages for different users (for example, if the package is unable to be delivered to a residence of the user or if the user otherwise desires to pick-up the package from the delivery locker system 100). The individual lockers may be provided such that a package associated with a first user may be stored within one locker, while a package associated with a second user may be stored within a different locker. This allows the users to access only their packages, while packages associated with other users remain secured in other lockers.

FIG. 1 also shows that the delivery locker system 100 includes a computing system 102. The computing system 102 may be a system that a user (for example, a user receiving a package or a delivery carrier delivering a package) may interact with to perform certain functions with respect to the delivery locker system 100. For example, computing system 102 may allow the user to enter a code that may trigger the delivery locker system 100 to unlock and/or open a particular delivery locker (e.g., unlock and/or open a locker door) including a package for the user.

The computing system 102 may include, for example, one or more input components, such as a keypad, a microphone, and/or any other type of component that may allow a user to provide input information to the computing system 102. For example, as illustrated further in FIGS. 2-3, the computing system 102 may include at least a physical keypad 103. The keypad 103 may be configured to receive inputs from a user, such as a selection of a combination of alphanumeric characters associated with the various keys of the keypad.

The computing system 102 may also allow a delivery carrier to perform deliveries at the delivery storage locker 100. For example, the computing system 102 may include a scanning device 107. A delivery carrier may scan a package using the scanning device 107 (for example, the scanning device 107 may be configured to scan a barcode located on the package) and then delivery locker system 100 may then unlock and/or open a particular locker. The delivery carrier may then place the package in the locker and shut the locker to secure the package within the delivery locker system 100. In some cases, the delivery locker system 100 may automatically shut the locker as well.

The computing system 102 may also include one or more sensors configured to receive information about the delivery locker system 100, the computing system 102, the protective covering 104, and/or the environment 101. For example, the figure shows at least a camera 105 that is provided on the computing system 102. However, any other types of sensors may also be provided, such as lidar, radar, ultra-wideband sensors, temperature sensors, and/or any other types of sensors that may be used to capture information. The information captured by the one or more sensors may be used for any number of purposes described herein or otherwise. For example, the information captured by the sensors may be used by a controller of the computing system 102 to facilitate any of the functionalities of the computing system 102 (the controller is described in additional detail with respect to FIG. 5).

Figure 5:
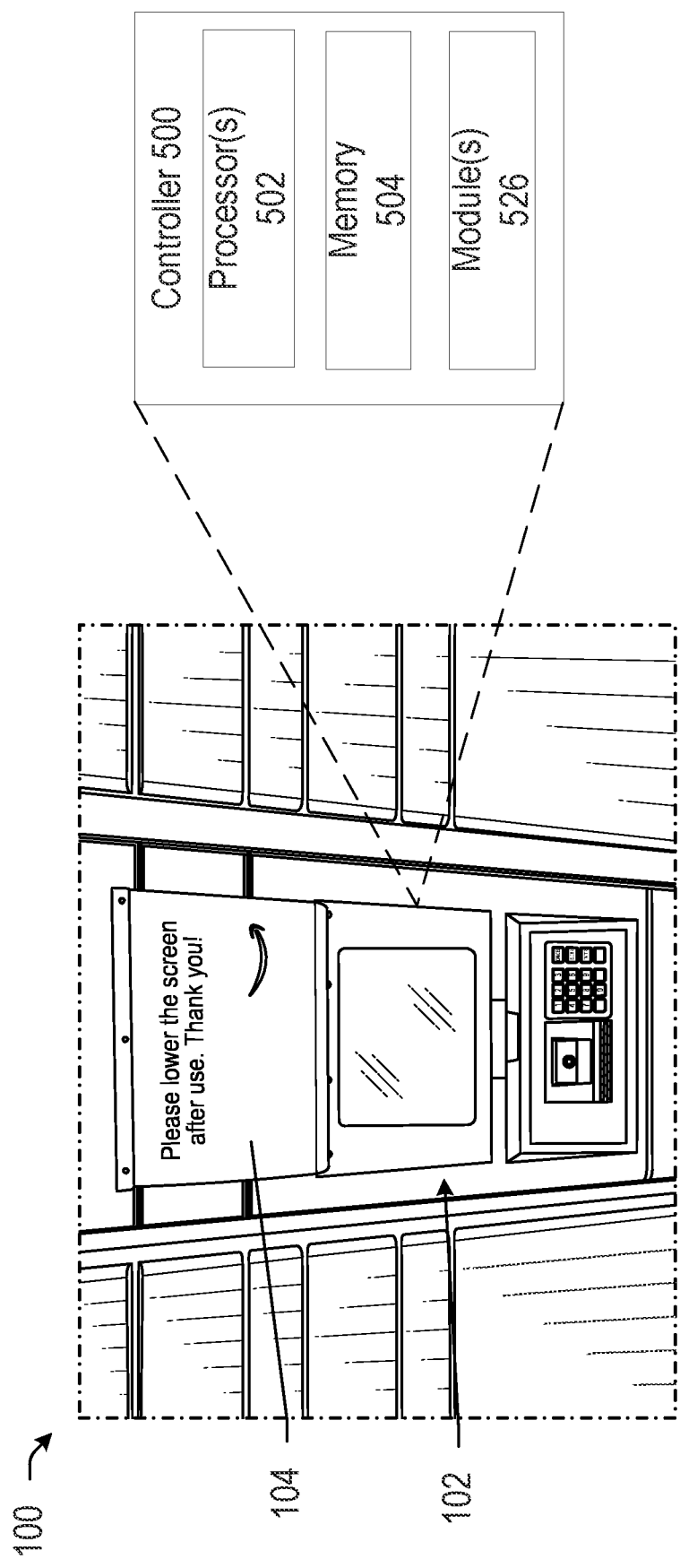
FIG. 5 illustrates an example controller of a delivery locker system in accordance with one or more example embodiments of the disclosure.

The computing system 102 may also include a display screen (which may be a touchscreen, for example), which may also be configured to receive user inputs (for example, user touches) to facilitate functionality of the delivery locker system 100 and/or present information to the user. The display screen is not visible in FIGS. 1-2, but instead is hidden behind the protective covering 104. FIGS. 3 and 5-6 provide an illustration of the display screen itself.

The protective covering 104 reduces the exposure of the display screen to sun rays and other heat sources from the external environment 101 to prevent the display screen from overheating due to overexposure to such heat sources. The protective covering 104 may include any number of different types of materials. For example, in FIG. 1 the protective covering 104 is depicted as including a fabric or other type of light-weight material. However, the protective covering 104 may also include any other type of material as well. As another example, the protective covering 104 may include a more rigid material, such as a hard plastic, metal, or glass. The protective covering 104 may also be translucent or transparent to allow for the display screen to be viewed when the protective covering is in the down position. However, it may also be desirable for the protective covering to be opaque such that the display screen is not visible until the protective covering is moved to the up position.

Figure 2:
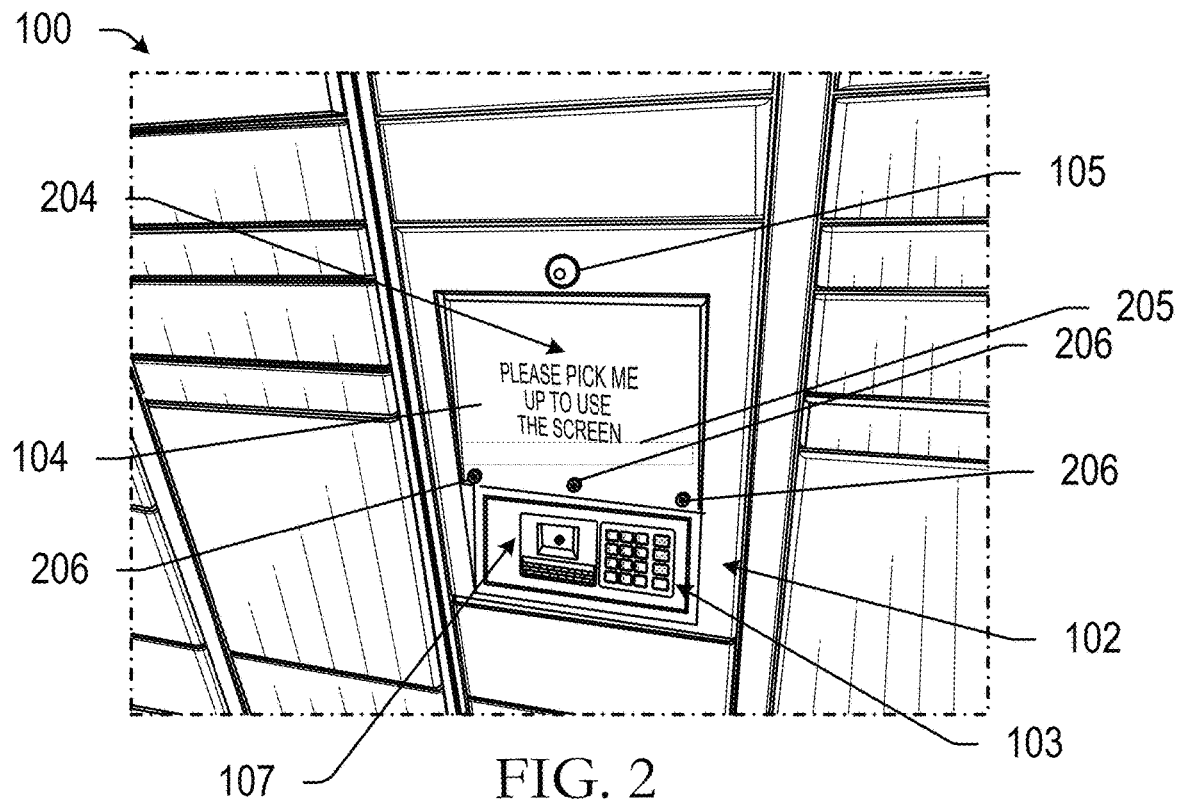
FIG. 2 illustrates another example protective covering in a down position in accordance with one or more example embodiments of the disclosure.
Figure 3:
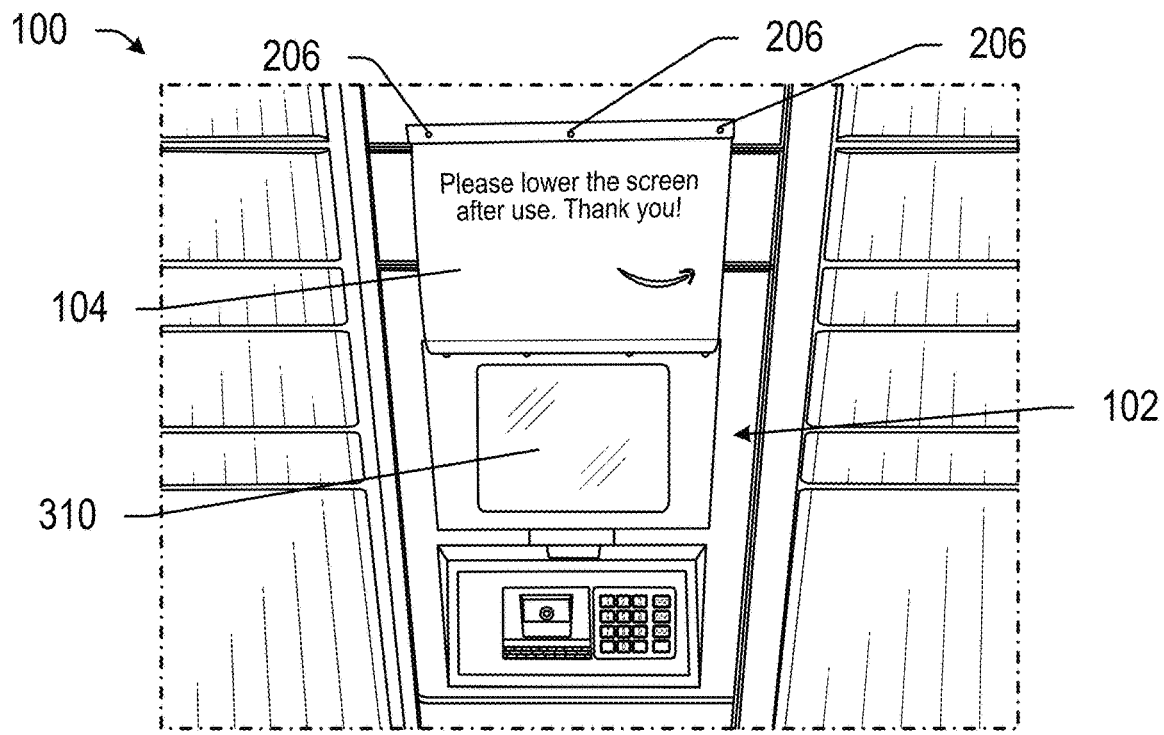
FIG. 3 illustrates another example protective covering in an up position in accordance with one or more example embodiments of the disclosure.

FIG. 2 illustrates another example protective covering in a down position in accordance with one or more example embodiments of the disclosure.

Particularly, FIG. 2 depicts a close-up view of the delivery locker system 100 and the protective covering 104 provided over the display screen (shown in FIGS. 3-4).

The protective covering 104 is also shown as having one or more magnets 206, which may be used to removably affix the protective covering to the delivery locker system 100 (e.g., the at least a portion of the delivery locker system 100 may include a metallic material). For example, the figure illustrates one example configuration in which the one or more magnets 206 specifically includes three magnets 206 that are provided on the bottom edge of the protective covering 104. When the protective covering 104 is in the down position (as shown in the figure), the one or more magnets 206 may removably affix the protective covering 104 to the delivery locker system 100 to prevent the protective covering from unintentionally moving. For example, the one or more magnets 206 may be used to maintain the protective covering 100 in its down position regardless of environmental conditions, such as wind.

The protective covering 100 is also shown as including specific messaging ("please pick me up to use the screen"). Although the messaging is depicted as being printed directly on the protective covering 104, the messaging may also be provided as digital messaging presented through a display integrated into the protective covering 104. For example, the display may be a seven-segment display, an LED display, an e-ink display, and/or any other type of display. The messaging may also be dynamic and may provide a number of different types of information to a use. For example, if the temperature of the display screen is above a threshold temperature (as described below), the display may indicate to the user 202 that the delivery locker system 100 may need to be accessed using a method other than an interaction with the display screen.

FIG. 3 illustrates another example protective covering 104 in an up position in accordance with one or more example embodiments of the disclosure.

With the protective covering 104 in the up position, the display screen 310 is made accessible to a user. The protective covering 104 may be maintained in the up position by removably affixing the one or more magnets 206 to the delivery locker system 100. As aforementioned, the use of the three delivery magnets 206 shown in FIG. 3 is merely exemplary and any other number of magnets 206 may be provided on the protective covering 104 in any other configuration. Additionally, a magnetic strip may be provided on the protective covering in place of individual magnets.

FIG. 3 also illustrates that the protective covering 104 may include a second message on the interior side of the protective covering 104 (e.g., the side that faces the display screen 310 when the protective covering 104 is in the down position. While FIGS. 2-3 illustrate that the protective covering 104 is moved vertically between a down position and an up position, the protective covering 104 may also be configured to be moved in front of and away from the display screen 310 in any other manner. For example, the protective covering 104 may be in an up position when the protective covering 104 is in front of the display screen 310 and may be moved to a down position below the display screen 310 when a user desires to interact with the displays screen 310. The protective covering 104 may also be configured to be moved horizontally to either side of the display screen 310. In further embodiments, the protective covering 104 may be configured to automatically retract in a similar manner to a window shade. If the protective covering 104 is provided as a rigid material, the protective covering 105 may be affixed to the delivery locker system on a hinge and the protective covering may be rotated about the hinge between the up and down position using a motor or servo. These are just a few non-limiting examples of ways in which the protective covering 104 may be configured to move in front of and away from the display screen 310.

Figure 4A:
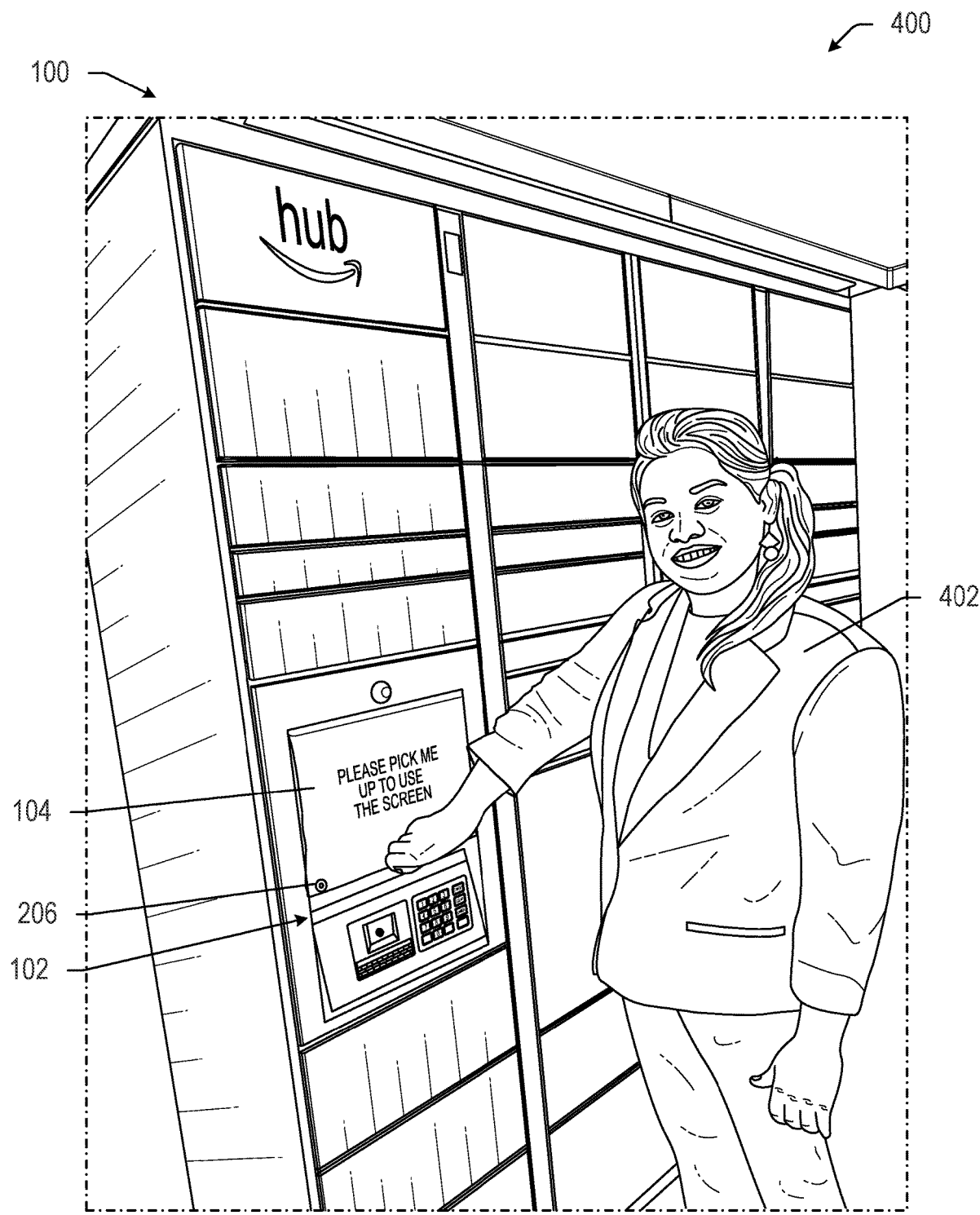
FIGS. 4A-4C illustrate an example use case in accordance with one or more example embodiments of the disclosure.
Figure 4B:
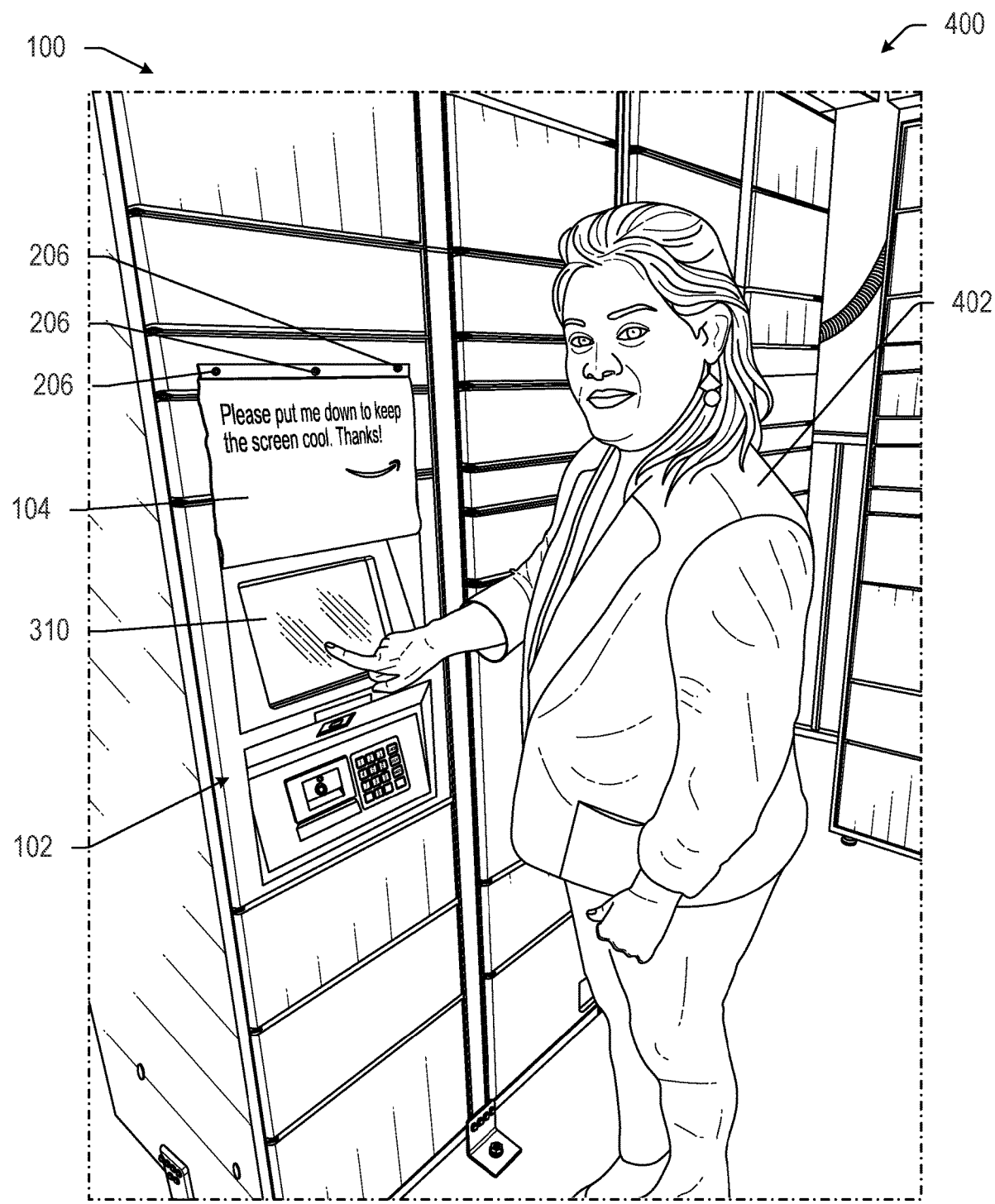
Figure 4C:

FIGS. 4A-4C illustrate an example use case 400 in accordance with one or more example embodiments of the disclosure. The use case 400 provides an illustration of one example scenario involving a user 202 interacting with the protective covering 104 to access the display screen of the computing system 102. For purposes of the use case 400, the user 402 may be at the delivery locker system 100 to pick up a package stored in one of the lockers, however, the delivery locker system 100 may also be accessed by a delivery carrier as well.

Beginning with FIG. 4A, the use case 400 shows a user 402 grasping a bottom edge of the protective covering 104 in preparation to move the protective covering 104 from the down position (shown in the figure) to the up position (shown in FIGS. 5-6). That is, the protective covering 104 is initially provided in the down position to provide protection to the display screen positioned behind the protective covering 104. In order to access the display screen, the user 202 may need to move the protective covering 104 from the down position to the up position.

Turning to, FIG. 4B the user 402 has moved the protective covering 104 from the down position to the up position. With the protective covering 104 in the up position, the display screen 310 is revealed to the user 402 and the user 402 may then interact with the displays screen 310. The one or more magnets 206 are shown as keeping the protective cover 104 removably affixed to a portion of the delivery locker system 100 located above the display screen 310 such that the protective cover 104 remains out of the way of the user 402 as the user interacts with the display screen 310.

Finally, FIG. 4C illustrates the user interacting with digital elements presented on the display screen 310. FIG. 4C shows that the display screen 310 may be a touchscreen display with which the user 202 may interact to perform various functions with respect to the delivery locker system 100. For example, the display screen 310 may display a digital keypad 406 and the user 202 may select a sequence of alphanumeric characters presented on the digital keypad 406 to enter a code used to access one of the lockers of the delivery locker system 100. The display screen 310 may also allow the user 402 to perform any other functions, such as pressing an element on the display screen 310 to open and/or close a particular locker door, view information about a delivery, return to a home screen, etc. The display screen 310 may also present information to the user 402, such as an identifier of a locker including the package for the user 402 and/or any other relevant information.

FIG. 5 illustrates an example controller 500 of a delivery locker system 100 in accordance with one or more example embodiments of the disclosure. As shown in the figure, the controller 500 may be provided within the computing system 102, however, the controller 500 may also be provided externally to the computing system 102 as well.

The memory 504 of the controller 500 may include volatile memory (memory that maintains its state when supplied with power) such as random-access memory (RAM) and/or non-volatile memory (memory that maintains its state even when not supplied with power) such as read-only memory (ROM), flash memory, ferroelectric RAM (FRAM), and so forth. Persistent data storage, as that term is used herein, may include non-volatile memory. In certain example embodiments, volatile memory may enable faster read/write access than non-volatile memory. However, in certain other example embodiments, certain types of non-volatile memory (e.g., FRAM) may enable faster read/write access than certain types of volatile memory.

In various implementations, the memory 504 may include multiple different types of memory such as various types of static random-access memory (SRAM), various types of dynamic random access memory (DRAM), various types of unalterable ROM, and/or writeable variants of ROM such as electrically erasable programmable read-only memory (EE-PROM), flash memory, and so forth. The memory 504 may include main memory as well as various forms of cache memory such as instruction cache(s), data cache(s), translation lookaside buffer(s) (TLBs), and so forth. Further, cache memory such as a data cache may be a multi-level cache organized as a hierarchy of one or more cache levels (L1, L2, etc.).

The data storage may include removable storage and/or non-removable storage including, but not limited to, magnetic storage, optical disk storage, and/or tape storage. The data storage may provide non-volatile storage of computer-executable instructions and other data. The memory 504 and the data storage, removable and/or non-removable, are examples of computer-readable storage media (CRSM) as that term is used herein.

The data storage may store computer-executable code, instructions, or the like that may be loadable into the memory 504 and executable by the processor(s) 502 to cause the processor(s) 502 to perform or initiate various operations. The data storage may additionally store data that may be copied to memory 504 for use by the processor(s) 502 during the execution of the computer-executable instructions. Moreover, output data generated as a result of execution of the computer-executable instructions by the processor(s) 502 may be stored initially in memory 504, and may ultimately be copied to data storage for non-volatile storage.

More specifically, the data storage may store one or more operating systems (O/S); one or more database management systems (DBMS); and one or more program module(s), applications, engines, computer-executable code, scripts, or the like such as, for example, one or more module(s) 526. Some or all of these module(s) may be sub-module(s). Any of the components depicted as being stored in data storage may include any combination of software, firmware, and/or hardware. The software and/or firmware may include computer-executable code, instructions, or the like that may be loaded into the memory 504 for execution by one or more of the processor(s) 502. Any of the components depicted as being stored in data storage may support the functionality described in reference to correspondingly named components earlier in this disclosure.

The data storage may further store various types of data utilized by components of the controller 500. Any data stored in the data storage may be loaded into the memory 504 for use by the processor(s) 502 in executing computer-executable code. In addition, any data depicted as being stored in the data storage may potentially be stored in one or more datastore(s) and may be accessed via the DBMS and loaded in the memory 504 for use by the processor(s) 502 in executing computer-executable code. The datastore(s) may include, but are not limited to, databases (e.g., relational, object-oriented, etc.), file systems, flat files, distributed datastores in which data is stored on more than one node of a computer network, peer-to-peer network datastores, or the like. In FIG. 5, the datastore(s) may include, for example, purchase history information, user action information, user profile information, a database linking search queries and user actions, and other information.

The processor(s) 502 may be configured to access the memory 504 and execute computer-executable instructions loaded therein. For example, the processor(s) 502 may be configured to execute computer-executable instructions of the various program module(s), applications, engines, or the like of the controller 500 to cause or facilitate various operations to be performed in accordance with one or more embodiments of the disclosure. The processor(s) 502 may include any suitable processing unit capable of accepting data as input, processing the input data in accordance with stored computer-executable instructions, and generating output data. The processor(s) 502 may include any type of suitable processing unit including, but not limited to, a central processing unit, a microprocessor, a Reduced Instruction Set Computer (RISC) microprocessor, a Complex Instruction Set Computer (CISC) microprocessor, a microcontroller, an Application Specific Integrated Circuit (ASIC), a Field-Programmable Gate Array (FPGA), a System-on-a-Chip (SoC), a digital signal processor (DSP), and so forth. Further, the processor(s) 502 may have any suitable microarchitecture design that includes any number of constituent components such as, for example, registers, multiplexers, arithmetic logic units, cache controllers for controlling read/write operations to cache memory, branch predictors, or the like. The microarchitecture design of the processor(s) 502 may be capable of supporting any of a variety of instruction sets.

Referring now to functionality supported by the various program module(s) depicted in FIG. 5, the module(s) 526 may include computer-executable instructions, code, or the like that responsive to execution by one or more of the processor(s) 502 may perform functions including, but not limited to, determine that a user is adjacent to a display screen, move a protective cover between different positions, activate an ultraviolet light assembly and/or a cooling system, unlock, lock, open and/or close a particular locker, transition a display screen to a low power mode or a high power mode, and/or perform any other functions associated with the computing system 102, delivery locker system 100, protective cover 104, and/or any other system device, component, etc. described herein or otherwise.

Referring now to other illustrative components depicted as being stored in the data storage, the O/S may be loaded from the data storage into the memory and may provide an interface between other application software executing on the controller 500 and the hardware resources of the controller 500. More specifically, the O/S may include a set of computer-executable instructions for managing the hardware resources of the controller 500 and for providing common services to other application programs (e.g., managing memory allocation among various application programs). In certain example embodiments, the O/S may control execution of the other program module(s) to dynamically enhance characters for content rendering. The O/S may include any operating system now known or which may be developed in the future including, but not limited to, any server operating system, any mainframe operating system, or any other proprietary or non-proprietary operating system.

The DBMS may be loaded into the memory 504 and may support functionality for accessing, retrieving, storing, and/or manipulating data stored in the memory 504 and/or data stored in the data storage. The DBMS may use any of a variety of database models (e.g., relational model, object model, etc.) and may support any of a variety of query languages. The DBMS may access data represented in one or more data schemas and stored in any suitable data repository including, but not limited to, databases (e.g., relational, object-oriented, etc.), file systems, flat files, distributed datastores in which data is stored on more than one node of a computer network, peer-to-peer network datastores, or the like. In those example embodiments in which the controller 500 is a mobile device, the DBMS may be any suitable light-weight DBMS optimized for performance on a mobile device.

Referring now to other illustrative components of the controller 500, module(s) 526 may include input/output (I/O) interface(s) may facilitate the receipt of input information by the controller 500 from one or more I/O devices as well as the output of information from the controller 500 to the one or more I/O devices. The I/O devices may include any of a variety of components, such as a display or display screen having a touch surface or touchscreen; an audio output device for producing sound, such as a speaker; an audio capture device, such as a microphone; an image and/or video capture device, such as a camera; a haptic unit; and so forth. Any of these components may be integrated into the controller 500 or may be separate. The I/O devices may further include, for example, any number of peripheral devices such as data storage devices, printing devices, and so forth.

It should be appreciated that the program module(s), applications, computer-executable instructions, code, or the like depicted in FIG. 5 as being stored in the data storage are merely illustrative and not exhaustive and that processing described as being supported by any particular module may alternatively be distributed across multiple module(s) or performed by a different module. In addition, various program module(s), script(s), plug-in(s), Application Programming Interface(s) (API(s)), or any other suitable computer-executable code hosted locally on the controller 500, and/or hosted on other computing device(s) accessible via one or more networks, may be provided to support functionality provided by the program module(s), applications, or computer-executable code depicted in FIG. 5 and/or additional or alternate functionality. Further, functionality may be modularized differently such that processing described as being supported collectively by the collection of program module(s) depicted in FIG. 5 may be performed by a fewer or greater number of module(s), or functionality described as being supported by any particular module may be supported, at least in part, by another module. In addition, program module(s) that support the functionality described herein may form part of one or more applications executable across any number of systems or devices in accordance with any suitable computing model such as, for example, a client-server model, a peer-to-peer model, and so forth. In addition, any of the functionality described as being supported by any of the program module(s) depicted in FIG. 5 may be implemented, at least partially, in hardware and/or firmware across any number of devices.

It should further be appreciated that the controller 500 may include alternate and/or additional hardware, software, or firmware components beyond those described or depicted without departing from the scope of the disclosure. More particularly, it should be appreciated that software, firmware, or hardware components depicted as forming part of the controller 500 are merely illustrative and that some components may not be present or additional components may be provided in various embodiments. While various illustrative program module(s) have been depicted and described as software module(s) stored in data storage, it should be appreciated that functionality described as being supported by the program module(s) may be enabled by any combination of hardware, software, and/or firmware. It should further be appreciated that each of the above-mentioned module(s) may, in various embodiments, represent a logical partitioning of supported functionality. This logical partitioning is depicted for ease of explanation of the functionality and may not be representative of the structure of software, hardware, and/or firmware for implementing the functionality. Accordingly, it should be appreciated that functionality described as being provided by a particular module may, in various embodiments, be provided at least in part by one or more other module(s). Further, one or more depicted module(s) may not be present in certain embodiments, while in other embodiments, additional module(s) not depicted may be present and may support at least a portion of the described functionality and/or additional functionality. Moreover, while certain module(s) may be depicted and described as sub-module(s) of another module, in certain embodiments, such module(s) may be provided as independent module(s) or as sub-module(s) of other module(s).

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

That which is claimed is:

1. A locker system comprising:
a housing;
a plurality of lockers disposed on a first side of the housing, wherein the plurality of lockers are individually accessible;
a display disposed on the first side of the housing, wherein the display is exposed to an ambient environment and is configured to receive touch input;
a cover disposed adjacent to the display, the cover having a first side facing an external environment and a second side facing the display, wherein the cover is configured to move from a first position in which the display is inaccessible to a second position in which the display is accessible;
a set of electromagnets coupled to the cover and configured to engage the housing when the display is in the second position;
a controller coupled to the display and configured to unlock individual lockers of the plurality of lockers, wherein the controller is configured to:
determine that the cover is moved to the second position; and
cause the set of electromagnets to be energized for a predetermined length of time.

2. The locker system of claim 1, further comprising:
a retractable mechanism configured to automatically retract the cover from the first position to the second position;
wherein the cover further comprises a wiper disposed on the second side of the cover, and wherein the wiper wipes the display while moving from the first position to the second position.

3. The locker system of claim 1, further comprising:
an ultraviolet light assembly coupled to the second side of the cover;
wherein the controller is configured to:
determine, at a first time interval, that that cover was moved to the first position from the second position; and
activate the ultraviolet light assembly for a period of time.

4. The locker system of claim 1, further comprising:
a motorized assembly configured to move the cover from the first position to the second position; and
a proximity sensor disposed adjacent to the display;
wherein the controller is configured to:
determine, using the proximity sensor, that a user is adjacent to the display; and
cause the motorized assembly to move the cover to the second position.

5. A system comprising:
a housing;
a locker door;
a display coupled to the housing, the display configured to receive touch input;
a controller configured to unlock the locker door;
a cover disposed adjacent to the display, the cover having a first side facing an external environment and a second side facing the display, wherein the cover is configured to move from a first position in which the display is inaccessible to a second position in which the display is accessible; and
a retractable mechanism configured to automatically retract the cover from the first position to the second position;
wherein the cover further comprises a wiper disposed on the second side of the cover, and wherein the wiper wipes the display while moving from the first position to the second position.

6. The system of claim 5, further comprising:
a set of electromagnets coupled to the cover and configured to engage the housing when the display is in the second position;
wherein the controller is configured to:
determine that the cover is moved to the second position; and
cause the set of electromagnets to be energized for a predetermined length of time.

7. The system of claim 5, wherein the cover further comprises:
one or more light emitting diodes disposed on the second side of the cover, wherein the one or more light emitting diodes are configured to present text.

8. The system of claim 5, wherein the display is configured to tilt with respect to the housing.

9. The system of claim 5, further comprising:
a wireless radio configured to connect to a user device;
wherein the controller is configured to:
determine the display is nonoperational; and
activate the wireless radio.

10. The system of claim 5, further comprising:
a motorized assembly configured to move the cover from the first position to the second position; and
a proximity sensor disposed adjacent to the display;
wherein the controller is configured to:
determine, using the proximity sensor, that a user is adjacent to the display; and
cause the motorized assembly to move the cover to the second position.

11. The system of claim 5, further comprising:
an ultraviolet light assembly coupled to the second side of the cover;
wherein the controller is configured to:
determine, at a first time interval, that that cover was moved to the first position from the second position; and
activate the ultraviolet light assembly for a period of time.

12. The system of claim 11, wherein the controller is further configured to:

determine, at a second time interval, that the cover was moved to the first position from the second position; and determine that an elapsed time since the ultraviolet light assembly was activated is less than a threshold.

13. The system of claim 5, further comprising:
a plurality of lockers configured to be unlocked via the display.

14. The system of claim 5, wherein the system is disposed in an outdoor environment.

15. An outdoor locker system comprising:
a housing;
a plurality of lockers;
a display coupled to the housing, the display configured to receive touch input;
a controller configured to unlock the plurality of lockers;
a cover disposed adjacent to the display, the cover having a first side facing an external environment and a second side facing the display, wherein the cover is configured to move from a first position in which the display is inaccessible to a second position in which the display is accessible; and
a set of electromagnets coupled to the cover and configured to engage the housing when the display is in the second position;
wherein the controller is further configured to:
determine that the cover is moved to the second position; and
cause the set of electromagnets to be energized for a predetermined length of time.

16. The outdoor locker system of claim 15, wherein the cover further comprises:
one or more light emitting diodes disposed on the second side of the cover, wherein the one or more light emitting diodes are configured to present text.

17. The outdoor locker system of claim 15, further comprising:
a wireless radio configured to connect to a user device;
wherein the controller is configured to:
determine the display is nonoperational; and
activate the wireless radio.

18. The outdoor locker system of claim 15, further comprising:
a motorized assembly configured to move the cover from the first position to the second position; and
a proximity sensor disposed adjacent to the display;
wherein the controller is configured to:
determine, using the proximity sensor, that a user is adjacent to the display; and
cause the motorized assembly to move the cover to the second position.

* * * * *